US009814829B2

(12) United States Patent
Zeltser et al.

(10) Patent No.: US 9,814,829 B2
(45) Date of Patent: *Nov. 14, 2017

(54) IMPLANTABLE BIOARTIFICIAL PERFUSION SYSTEM

(71) Applicants: Gregory Zeltser, Irvine, CA (US); Michael Piliavin, Los Angeles, CA (US)

(72) Inventors: Gregory Zeltser, Irvine, CA (US); Michael Piliavin, Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/753,554

(22) Filed: Jun. 29, 2015

(65) Prior Publication Data
US 2015/0297828 A1 Oct. 22, 2015

Related U.S. Application Data

(62) Division of application No. 13/835,655, filed on Mar. 15, 2013, now Pat. No. 9,101,707.
(Continued)

(51) Int. Cl.
*A61M 5/142* (2006.01)
*A61F 2/02* (2006.01)
(Continued)

(52) U.S. Cl.
CPC ......... *A61M 5/14276* (2013.01); *A61F 2/022* (2013.01); *A61M 1/28* (2013.01);
(Continued)

(58) Field of Classification Search
CPC .... A61M 5/14276; A61M 2005/14513; A61M 2205/3303; A61M 2205/7554; A61F 2/022; C12N 5/0677; A61K 2035/126
See application file for complete search history.

(56) References Cited

U.S. PATENT DOCUMENTS 4,332,893 A 6/1982 Rosenberg
4,378,016 A 3/1983 Loeb
(Continued)

FOREIGN PATENT DOCUMENTS

WO 98/50088 A1 11/1998
WO 9850088 A1 11/1998
WO 2011085180 A2 7/2011

OTHER PUBLICATIONS

European Office Action for related European Patent Application No. 16154674.2-1402 dated Mar. 4, 2016, 8 Pages.
(Continued)

*Primary Examiner* — Nathan R Price
*Assistant Examiner* — Justin L Zamory
(74) *Attorney, Agent, or Firm* — Ditthavong & Steiner, P.C.

(57) ABSTRACT

The disclosure provides an implantable bioartificial active secretion system for providing a physiological regulating secretion such as insulin necessary for functionality of a physiologic activity such as glucose metabolism of a living-being host. The system includes a housing implantable within the host, in fluidic communication with tissue fluid indicative of a physiological regulating secretion need. A chamber within the housing contains a plurality of physiologically active, autonomously functioning, live secretory cells for producing the physiological regulating secretion. A continually operating two pump apparatus moves tissue fluid into contact with the secretory cells for pick up of the physiological regulating secretion for subsequent physiologically-effective dispensing into the host, while avoiding immuno-rejection of the host body or of the host to the secretory cells.

9 Claims, 3 Drawing Sheets

Related U.S. Application Data (60) Provisional application No. 61/639,078, filed on Apr. 27, 2012.

(51) Int. Cl.
 *A61M 1/28* (2006.01)
 *A61M 5/145* (2006.01)

(52) U.S. Cl.
 CPC ............ *A61M 2005/14513* (2013.01); *A61M 2202/0007* (2013.01); *A61M 2205/04* (2013.01); *A61M 2205/18* (2013.01); *A61M 2205/3303* (2013.01); *A61M 2205/3523* (2013.01); *A61M 2210/1021* (2013.01)

(56) References Cited

U.S. PATENT DOCUMENTS

| | | |
|---|---|---|
| 4,944,659 A | 7/1990 | Labbe et al. |
| 4,952,406 A | 8/1990 | Brown et al. |
| 5,011,472 A | 4/1991 | Aebischer et al. |
| 5,045,082 A | 9/1991 | Ayer et al. |
| 5,116,493 A | 5/1992 | Chick et al. |
| 5,141,631 A | 8/1992 | Whitman |
| 5,262,055 A * | 11/1993 | Bae .................. A61F 2/022 210/321.75 |
| 5,554,148 A | 9/1996 | Aebischer et al. |
| 5,855,616 A | 1/1999 | Fournier et al. |
| 5,972,369 A | 10/1999 | Roorda et al. |
| 5,993,414 A | 11/1999 | Haller |
| 6,123,861 A | 9/2000 | Santini, Jr. et al. |
| 6,475,750 B1 | 11/2002 | Han et al. |
| 6,511,473 B2 | 1/2003 | Bartha et al. |
| 6,627,422 B1 | 9/2003 | Li et al. |
| 6,730,315 B2 | 5/2004 | Usala et al. |
| 7,651,696 B2 | 1/2010 | Bates |
| 8,048,419 B2 | 11/2011 | Humes |
| 8,109,923 B2 | 2/2012 | Hood et al. |
| 8,224,425 B2 | 7/2012 | Freeman et al. |
| 8,277,713 B2 | 10/2012 | Petisce et al. |
| 8,304,849 B2 | 11/2012 | Dishongh et al. |
| 8,315,681 B2 | 11/2012 | Kanayama et al. |
| 8,346,338 B2 | 1/2013 | Goode, Jr. et al. |
| 2002/0103475 A1* | 8/2002 | Bartha .................. C12N 5/0677 604/891.1 |
| 2004/0124147 A1* | 7/2004 | Fissell, IV .......... A61M 1/3489 210/650 |
| 2009/0032469 A1* | 2/2009 | Panzani ................ B01D 29/21 210/646 |
| 2009/0041825 A1 | 2/2009 | Kotov et al. |
| 2011/0142700 A1 | 6/2011 | Gura et al. |

OTHER PUBLICATIONS

Cobelli et al., "Artificial Pancreas: Past, Present, Future", Diabetes, Nov. 1, 2011, vol. 60, No. 11, retrieved on Feb. 25, 2016 from http://diabetes.diabetesjournals.org/content/60/11/2672.full. pdf+html, pp. 2672-2682.

Zekorn et al., "Lymphoid activation by micro- and macroencapsulated islets during mixed lymphocyte islet culture", Acta Diabetologica, Feb. 1993, 30(4), pp. 238-242.

Zekorn et al., "Synergistic effect of microencapsulation and immunoalteration on islet allograft survival in bioartificial pancreas", J. Mol Med, Jan. 1999, 77(1), pp. 193-198.

Zimmermann et al., "Towards a medically approved technology for alginate-based microcapsules allowing long-term immunoisolated transplantation", J Mater Sci Mater Med., Jun. 2005, 16(6), pp. 491-501.

Notification of Transmittal of The International Search Report and the Written Opinion of the International Searching Authority, or the Declaration; International Search report for related International Application No. PCT/US13/38133, 5 pages.

Barkai et al., "Enhanced oxygen supply improves islet viability in a new bioartificial pancreas", Cell Transplant, Oct. 3, 2012, 51 Pages.

Bellin et al., "Similar islet function in islet allotransplant and autotransplant recipients, despite lower islet mass in autotransplants", Transplantation, Feb. 15, 2011, pp. 367-372.

Bunger et al., "Biocompatibility and surface structure of chemically modified immunoisolating alginate-PLL capsules", J Biomed Mater Res 67A, Nov. 6, 2003, pp. 1219-1227.

Calafiore et al., "Grafts of microencapsulated pancreatic islet cells for the therapy of diabetes mellitus in non-immunosuppressed animals", Biotechnol Appl Biochem, Apr. 2004, pp. 159-164.

Calafiore et al., "Microencapsulated Pancreatic Islet Allografts Into Nonimmunosuppressed Patients With Type 1 Diabetes", Diabetes Care, Jan. 29, 2006, vol. 29, No. 1, pp. 137-138.

Chae et al., "Protection of insulin secreting cells from nitric oxide induced cellular damage by crosslinked hemoglobin", Biomaterials, Feb. 2004, vol. 25, No. 5, pp. 843-850.

Darrabie et al., "Characteristics of poly-L-ornithine coated alginate microcapsules", Biomaterials, Dec. 2005, 26(34). pp. 6846-6852.

Delunay et al., "Glucose-Insulin Kinetics of a Bioartificial Pancreas Made of an AN69 Hydrogel Hollow Fiber Containing Porcine Islets and Implanted in Diabetic Mice", Artificial Organs, Apr. 1998, 22(4), pp. 291-299.

Vos et al., "Alginate-based microcapsules for immunoisolation of pancreatic islets", Biomaterials, Nov. 2006, 27(32), pp. 5603-5617.

Dufrane et al., "Six-month survival of microencapsulated pig islets and alginate biocompatibility in primates: Proof of concept", Transplantation, May 15, 2006, 81(9), pp. 1345-1353.

Dufrane et al., "The influence of implantation site on the biocompatibility and survival of alginate encapsulated pig islets in rats", Biomaterials, Feb. 23, 2006, 27(17), pp. 3201-3208.

Dufrane et al., "Macro- or microencapsulation of pig islets to cure type 1 diabetes", World J Gastroenterol, Dec. 21, 2012, 18(47), pp. 6885-6893.

Elliott et al., "Live encapsulated porcine islets from a Type 1 diabetic patient 9.5 yr after xenotransplantation", Xenotransplantation, Mar. 2007, 14(2), pp. 157-161.

Giraldo et al., "Enhancing Clinical Islet Transplantation through Tissue Engineering Strategies", Journal of Diabetes Science and Technology, Sep. 1, 2010, 4(5), pp. 1238-1247.

Hunter et al., "Encapsulated beta-islet cells as a bioartificial pancreas to treat insulin-dependent diabetes during pregnancy", Am. J. Obstet Gynecol, Oct. 1997, 177(4), pp. 746-752.

Hunter et al., "Bioartificial Pancreas Use in Diabetic Pregnancy", ASAIO Journal, Jan. 1, 1999, 45(1), pp. 13-17.

Thevissen et al., "Sustained function of alginate-encapsulated human islet cell implants in the peritoneal cavity of mice leading to a pilot study in a type 1 diabetic patient", Diabetologia, Apr. 26, 2013, 56(7), 10 Pages.

Jaremko et al., "Advances Toward the Implantable Artificial Pancreas for Treatment of Diabetes", Diabetes Care, Mar. 1998, 21(3), pp. 444-450.

Kizilel et al., "Encapsulation of pancreatic islets within nano-thin functional polyethylene glycol coatings for enhanced insulin secretion", Tissue Eng. Part A, Jul. 2010, 16(7), pp. 2217-2228.

Krishnan et al., "Cellular Immunoisolation for Islet Transplantation by a Novel Dual Porosity Electrospun Membrane", Transplantation Proceedings, Nov. 2011, 43(9), pp. 3256-3261.

Lacy et al., "Activation of Intraislet Lymphoid Cells Causes destruction of Islet Cells", Am. J. Pathol., May 1991, 138(5), pp. 1183-1190.

Lai et al., "Vascular endothelial growth factor increases functional beta-cell mass by improvement of angiogenesis of isolated human and murine pancreatic islets", Transplantation, Jun. 15, 2005, 79(11), pp. 1530-1536.

Lamb et al., "Function and Viability of Human Islets Encapsulated in Alginate Sheets: In Vitro and in Vivo Culture", Transplantation Proceedings, Nov. 2011, 43(9), pp. 3265-3266.

McQuilling et al., "New Alginate Microcapsule System for Angiogenic Protein Delivery and Immunoisolation of Islets for Transplantation in the Rat Omentum Pouch", Transplantation Proceedings, Nov. 2011, vol. 43, No. 9, pp. 3262-3264.

(56) References Cited

OTHER PUBLICATIONS

Moya et al., "Fibroblast growth factor-1 (FGF-1) loaded microbeads enhance local capillary neovascularization", J Surg Res, 2010, 160(2), pp. 208-212.

Moya et al., "The effect of FGF-1 loaded alginate microbeads on neovascularization and adipogenesis in a vascular pedicle model of adipose tissue engineering", Biomaterials, Jan. 18, 2010, 31(10), pp. 2816-2826.

Narang et al., "Biological and biomaterial approaches for improved islet transplantation", Pharmacol Reviews, Jun. 2006, 58(2), pp. 194-243.

Nathan et al., "Postprandial insulin profiles with implantable pump therapy may explain decreased frequency of severe hypoglycemia, compared with intensive subcutaneous regimens, in insulin-dependent diabetes mellitus patients", Am. J. Med., Apr. 1996, 100(4), pp. 412-417.

Omer et al., "Survival and maturation of microencapsulated porcine neonatal pancreatic cell clusters transplanted into immunocompetent diabetic mice", Diabetes, Jan. 2003, 52(1), pp. 69-75.

Omer et al., "Long-term normoglycemia in rats receiving transplants with encapsulated islets", Transplantation, Jan. 15, 2005, 79(1), pp. 52-58.

Opara et al., "Design of a bioartificial pancreas", J Investig Med., Oct. 2010, vol. 58, No. 7, pp. 831-837.

O'Sullivan et al., "Islets transplanted in immunoisolation devices: a review of the progress and the challenges that remain", Endocr Rev., Sep. 27, 2011, 32(6), pp. 827-844.

Pareta et al., "Design of a bioartificial pancreas", Pathobiology, May 6, 2013, 58(7), pp. 194-202.

Qi et al., "Survival of human islets in microbeads containing high guluronic acid alginate crosslinked with Ca2+ and Ba2+", Xenotransplantation, Nov.-Dec. 2012, vol. 19, No. 6, pp. 355-364.

Renard et al., "Closed-Loop Insulin Delivery Using a Subcutaneous Glucose Sensor and Intraperitoneal Insulin Delivery", Diabetes Care, 2010, vol. 33, pp. 121-127.

Reynoso et al., "Short- and long-term outcome for living pancreas donors", J Hepatobiliary Pancreat Sci, Aug. 4, 2010, 17(2), pp. 92-96.

Rickels et al., "β-Cell Function Following Human Islet Transplantation for Type 1 Diabetes", Diabetes, 2005, vol. 54, pp. 100-106.

Rolland et al., "Insulin Secretion of Free and AN69 Encapsulated Islets", Transplant Proc., Jun. 1997, 29(4), pp. 2140-2141.

Schneider et al., "Long-Term Graft Function of Adult Rat and Human Islets Encapsulated in Novel Alginate-Based Microcapsules After Transplantation in Immunocompetent Diabetic Mice", Diabetes, Mar. 2005, 54(3), pp. 687-693.

Tendulkar et al., "A scalable microfluidic device for the mass production of microencapsulated islets", Transplantation Proceedings, Nov. 2011, 43(9), pp. 3184-3187.

Thompson et al., "Reduced progression of diabetic microvascular complications with islet cell transplantation compared with intensive medical therapy", Transplantation, Feb. 15, 2011, 91(3), pp. 373-378.

Tuch et al., "Safety and Viability of Microencapsulated Human Islets Transplanted Into Diabetic Humans", Diabetes Care, Jun. 23, 2009, 32(10), pp. 1887-1889.

Udelsman et al., "Implanted programmable insulin pumps: One hundred fifty-three patient years of surgical experience", Surgery, Dec. 1997, 122(6), pp. 1005-1011.

Wang et al., "Successful allotransplantation of encapsulated islets in pancreatectomized canines for diabetic management without the use of immunosuppression", Transplantation, Feb. 15, 2008, 85(3), pp. 331-337.

Weinhart et al., "Linear Poly(methyl glycerol) and Linear Polyglycerol as Potent Protein and Cell Resistant Alternatives to Poly(ethylene glycol)", Chem. Asian J., Sep. 3, 2010, 5(9), pp. 1992-2000.

Woods et al., "Permeability characteristics of microencapsulated pancreatic islets", Transplant Proc., Jun. 1997, 29(4), 1 Page.

Wu et al., "Assessment of the protective effect of uncoated alginate microspheres", Transplant Proc., Jun. 1997, 29(4), pp. 2146-2147.

Yang et al., "The cytoprotection of chitosan based hydrogels in xenogeneic islet transplantation: An in vivo study in streptozotocin-induced diabetic mouse", Biochem Biophys Res Commun., Feb. 18, 2010, 393(4), pp. 818-823.

Yao et al., "Dynamic aspects for interislet synchronization of oscillatory insulin secretions", Am.J. Physiol., Jun. 1, 1997, 272(6 Pt 1), pp. E981-E988.

\* cited by examiner

IMPLANTABLE BIOARTIFICIAL PERFUSION SYSTEM

CROSS REFERENCE TO RELATED APPLICATIONS

This application is a divisional application of U.S. patent application Ser. No. 13/835,655, now U.S. Pat. No. 9,101,707, titled "Implantable Bioartificial Perfusion System," filed on Mar. 15, 2013, which claims the benefit of priority under 35 U.S.C. §119(e) to U.S. Provisional Application No. 61/639,078, titled "Implantable Bioartificial Active Insulin Dispenser for Diabetes Control," filed on Apr. 27, 2012, the entire disclosure of each of which is hereby incorporated by reference in its entirety for all purposes.

FIELD OF THE INVENTION

The present invention relates in general to implantable devices for providing medically required treatment regimens over a period of time, and in particular to an implantable bioartificial perfusion system containing live secretory cells that provide a physiologically-required secretion to a living-being host patient in response to specific respective needs of the patient as determined by the live secretory cells in response to physiological make-up of host tissue fluid in contact with the secretory cells.

BACKGROUND OF THE INVENTION

Natural production of numerous agents, metabolites, enzymes, and other secretions occur within a living being host as physiological events take place. One such event is the metabolism of carbohydrates to glucose, which is mainly controlled by insulin produced by the beta cells of the islets of Langerhans within the pancreas. Insulin is necessary in maintaining glucose homeostasis. In addition to its principal role in carbohydrate metabolism, insulin also significantly affects lipid, protein, and mineral metabolism. When efficient insulin production by the pancreas is inhibited or terminated and therefore is insufficient, as occurs substantially in Type I diabetes, for example, where immune system of the host destroys beta cells of the islets of Langerhans, insulin from another source must be provided or the affected individual will suffer from many severe consequences of diabetes mellitus. The dispensation of medicament is determined by live secretory cells in response to physiological make-up of host tissue fluid in contact with the secretory cells. Thus, in the case of a diabetes patient, insulin would be dispensed whereas chemotherapeutic drugs would be dispensed in the case of cancer. In these and other similar circumstances, it is highly beneficial to the patient when automatic dispensing of the medicament occurs, without the need to resort to pills, injections or other discomforting means of medication. A special unit can be implanted within the patient. This unit consists of a reservoir of living cells, of type determined by patient's needs, and the live cells act in response to the body fluids perfusing through them. The implanted unit will have a supply of live cells that will be active for 4 years, a micropump and associated electronics to circulate the perfusion fluid, a wireless transmitter to communicate with the unit and an inductively rechargeable battery.

Prior-art approaches for providing insulin to maintain proper plasma glucose concentrations are numerous. One of the most commonly employed approaches is the injection of insulin into the patient a plurality of times daily in response to plasma-glucose monitoring. Subcutaneous injection is a usual insulin introduction route, but is flawed and/or disfavored for several reasons. In particular, injection administration is limited because there is no direct feedback between blood glucose level and the dosage of insulin. In addition, there is poor patient acceptance, significant absorption variability among patients, potential overdosing resulting in hyperinsulinemia/hypoglycemia, potential underdosing resulting in hypoinsulinemia/hyperglycemia, formation of anti-insulin antibodies, hypersensitivity reactions due to insulin formulations, and other untoward occurrences. Relatively new jet injector devices, as opposed to traditional syringes, do not appreciably avoid syringe-injection limitations as noted above. Orally administered insulin finds poor effectiveness because of the vast variability found in digestive processes and digestion states among patients.

Another prior art approach for providing insulin to patients is the use of wearable or implantable insulin pumps, which are pre-programmed and pre-loaded with insulin and do not allow direct feedback of the optimal dosage. These pumps can also cause both mechanical and physiological problems for the patient. With respect to the former problem, these pumps can experience catheter blockage, infection, skin inflammation, erosion, local fluid accumulation, dislocation due to patient physical activity, and required regular refills of insulin usually at monthly or bimonthly intervals. With respect to the latter problem, presently available insulin pumps do not have reliable glucose sensors and therefore, are unable to precisely dispense a needed insulin quantity for proper plasma-glucose level maintenance. In addition, presently available insulin pumps do not have reliable glucose sensors and therefore, are unable to precisely dispense a needed insulin quantity for proper plasma-glucose level maintenance.

New methods for treating insulin-dependent diabetes mellitus are presently being sought. Although it is possible to transplant a pancreas from one human to another, the survival rate for this procedure is only 40% at one year following surgery. Researchers have also used isolated pancreatic islets in transplantation approaches in attempts to find a viable long term treatment of diabetes.

The islets of Langerhans are clusters of differentiated cells sharing a common precursor. Found in the pancreas of mammals, islet cells taken together can be considered as a single endocrine organ. The islet cells occupy about 7% of the human pancreas, which also contains the exocrine acinar tissue. The composition of cells in the islets differ depending on the location of the islet in the pancreas. Central to each islet is a core of insulin secreting beta cells. Surrounding the beta cells are somatostatin secreting delta cells, glucagon secreting alpha cells and pancreatic polypeptides containing F-cells. Alpha cells tend to be concentrated in the tail and the body of the pancreas whereas the F-cells are concentrated in the head. This distribution corresponds to the embryonic origin of alpha and F-cells from dorsal and ventral primordium of the pancreas. Transplantation of pancreatic beta cells has been done to the pancreas, liver, muscles, or peritoneal cavity of the patient, or the transplantation of an entire donor-pancreas as a replacement. Such an approach, however, is not practical because of recipient immune-rejection, limited availability of donor organs, and other restraints on patient acceptance.

In view of the above inability of prior art approaches to artificially provide a natural imitation of a physiological secretion, it is apparent that highly important and unfulfilled needs exist first for sensing an in vivo demand for a secretory product; and second for fulfilling that requirement by providing an appropriate quantity of secretory product.

SUMMARY OF THE INVENTION

The present invention addresses these needs and more by providing an implantable bioartificial perfusion system for providing a physiological secretion necessary for the functionality of a physiologic activity of a living-being host. The system includes a housing having chamber with a biocompatible porous tissue scaffold to maintain the viability and functional activity of the cells of the islets of Langerhans, and which is in fluidic communication with an inlet and an outlet. The inlet includes an external opening thereto, and the outlet includes an external opening therefrom. The housing is implantable at least partially within the host such that the inlet and outlet openings are placed in fluidic communication with the tissue fluid of the host. The tissue fluid can be received into the housing and thereafter dispensed from the housing. A chamber is disposed within the housing between the inlet and outlet and in communication therewith, and contains a biocompatible tissue scaffold or similar framework, filled with a plurality of physiologically active, autonomously and in concert functioning, live secretory cells for producing the physiological secretion. Also disposed within the housing is a continuously-operating two pump apparatus located upstream and downstream of the chamber for drawing initial tissue fluid through the inlet from the host for contact with the physiologically active cells within the chamber for pick up and regulation of the physiological secretion, and for dispensing the resulting tissue fluid bearing the physiological secretion through the outlet and back into the host. The inlet and outlet filter systems are in operational communication with the external openings of the inlet and outlet, and have openings therethrough sized for prohibiting passage of immune system cells, immunoglobulins, and complement system components of the host.

The tissue fluid drawn to be in contact with the live secretory cells must generally reflect host requirements for the particular physiological secretion. Thus, in treating diabetes for example, peritoneal fluid is drawn since it is known that peritoneal fluid reflects blood glucose levels, whereby peritoneal fluid contacts secretory cells that are pancreatic beta cells that produce insulin for peritoneal-fluid uptake and return for routing to regulate glucose levels. The secretory cells may be immune isolated, using a permeable medium through which cellular nutrient as well as cellular metabolic waste can pass and likewise, through which the physiological secretion can pass, but not through which immune system cells can pass on the off-chance that such cells may be passed through the inlet filter. Immunoisolation and use of the porous scaffold increases the loading density of the cells and their surface interaction with the fluid as well as signal communication among cells. Depending upon the specific application, secretory-cell life span many times can be up to about four years, after which time replacement cells may be introduced.

The two pump apparatus may be located upstream and downstream from the chamber moving there within the initial tissue fluid and the tissue fluid bearing the physiological secretion through the housing. Simultaneously, the arrangement of the plurality of secretory cells is such that sub-pluralities thereof are disposed on a three-dimensional scaffold, wherein a plurality of the scaffolds may be situated into a pile. To prevent and clean the inlet and outlet nanofilters from accumulating and clogging cellular and extracellular matrix material, a double back flush hydraulic mechanism can be used. The pumping can be accomplished electromagnetically, by osmotic, electro-osmotic, peristaltic or other pumping methods and may be controlled by a programmed controller or special circuit disposed within the housing and thus implanted. The tissue fluid reflects whether a need is present for the particular secretion provided by the secretory cells (e.g., glucose level for insulin-secreting cells), whereby the secretory cells will naturally respond to the conveyed need and automatically produce a quantity of secretion specific to this need as sensed by the secretory cells. This secretion is picked up by the tissue fluid as it contacts the secretory cells, and thereafter is delivered within the host. When the tissue fluid indicates less need for the secretion (e.g., the required activity of the secretion has been completed for the time being), such reduced need is sensed by the secretory cells as the tissue fluid continues in contact therewith, and the secretory activity naturally reduce their secretion or cease until the next demand for secretion is sensed.

The implantable device, containing a microcontroller and/or other appropriate circuitry will communicate to the external environment by wireless means. The circuitry will provide data to the host locally on a wearable display system as well as have an optional capability to send information over the internet. To reduce bandwidth requirements, the communication system will take advantage of data compression or coding.

An optional new application of the self-charging mechanism (employed in electronic automatic quartz watches) using a weighted rotor to turn a tiny electrical generator, charging a rechargeable battery when the patient with IBPS is moving. The battery powers the control unit, the pump, and circuitry. Alternatively, the electronic control and wireless circuits will be powered by mini or micro sized rechargeable batteries. Included in the circuit will be means by which the batteries will be inductively rechargeable, without having to remove the device from the patient.

A novel miniature pump will provide a constant flow of the peritoneal fluid through the IBPS. The pump used for this purpose may be based on a variety of existing pumps and technologies in existence, such electroosmotic, dielectrophoretic, micro sized mechanisms, piezoelectrics, etc. Depending on the pump type and action, the pumps are placed accordingly through the system at appropriate locations. In particular, an innovation for this system is the use of a peristaltic pump, with no moving parts to perform the peristaltic motion necessary for transport of the peritoneal fluid through the system and the pumps are an integrated part of the scaffold or islet containing base unit.

A miniature glucose sensor will control and assure proper operation. If the concentration of the glucose will be higher than normal level, it will set off an alarm and the doctor will decide either to increase flow velocity, or add insulin injections, or replace the implantable device.

A miniature liquid flow sensor will monitor flow rate of a tissue fluid such as peritoneal fluid and activate back-flash mechanism via microprocessor when the flow rate is below an acceptable level. If the back-flash does not help it will set off an alarm and the doctor should replace the implantable device.

A novel method for islets viability monitoring is a simple, reliable and long lasting technique based on identification of the critical pH<7.35 signaling death of the islet cells. In this case the doctor should immediately replace the implantable device.

A control circuit with or without wireless capabilities, will monitor and display glucose concentration, pH value and flow velocity on a small graphical user interface (GUI) display placed on the patient's wrist The same data will also be available to any other device capable of receiving data from the implanted unit. The control circuit will automatically activate the back-flush mechanism and set off an alarm in case of (1) abnormal tissue fluid flow rate; (2) abnormal glucose level; or (3) massive cell death. In the case of massive cell death the microprocessor will stop the pump in the failed unit and the other unit will take over. The data will be immediately sent wirelessly to the external monitoring devices. When any alarm is triggered, whether from a high glucose concentration or massive cell death, or any condition which is not desirable, the patient should immediately seek medical help from a professional.

As is apparent, the implantable bioartificial perfusion system herein described significantly replicates natural metabolic function by employing live secretory cells as both sensor and provider of physiologic balance. Such live-cell employment eliminates external guess work with respect to quantity and timing of secretion-product injection or other type introduction since actual cells make a natural determination of need followed by a natural production and natural release of an exactly-necessary quantity of the secretory product.

BRIEF DESCRIPTION OF THE DRAWINGS

An illustrative embodiment of the invention is shown in the accompanying drawings in which.

DETAILED DESCRIPTION OF THE INVENTION

Unless otherwise defined, scientific and technical terms used in connection with the disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

In one embodiment, the disclosure provides an implantable bioartificial perfusion system for providing a physiological regulating secretion necessary for functionality of a physiologic activity of a living-being host, the system comprising:

a) a housing having an inlet with an external opening thereto and an outlet with an external opening therefrom, the housing implantable at least partially within the host such that the inlet and outlet openings are placed in fluidic communication with tissue fluid of the host for receiving into and dispensing from the housing the tissue fluid;

b) a chamber disposed within the housing between the inlet and outlet and in communication therewith, the chamber having therein a plurality of physiologically active, autonomously and in concert functioning, live secretory cells for producing the physiological secretion;

c) a constantly operating two pump apparatus for drawing initial tissue fluid through the inlet from the host for contact with the physiologically active cells within the chamber for pick up of the physiological secretion, and for dispensing resulting tissue fluid bearing the physiological secretion through the outlet and into the host; and d) an inlet filter in operational communication with the external opening of the inlet and disposed upstream of the chamber, wherein the inlet filter comprises a plurality of mesh woven polymer yarn to collect peritoneal fluid from a high surface area of the parietal peritoneum and visceral peritoneum by means of capillary forces and a size-exclusion membrane filter separated from the plurality of mesh woven polymer yarn by a capillary gap for prohibiting passage into the chamber of immune system cells of the host.

In one aspect, the disclosure provides an implantable bioartificial perfusion system for providing a physiological regulating secretion necessary for functionality of a physiologic activity of a living-being host, wherein the two pump apparatus are located upstream and downstream from the chamber, and wherein the two pump apparatus uses electromagnetic, osmotic, or electro-osmotic force.

In another aspect, the disclosure provides an implantable bioartificial perfusion system for providing a physiological regulating secretion necessary for functionality of a physiologic activity of a living-being host, further comprising an outlet filter in operational communication with the external opening of the outlet and disposed downstream of the chamber, wherein the outlet filter comprises pores therethrough sized for prohibiting passage into the chamber of immune system cells of the host.

In another embodiment, the disclosure provides an implantable bioartificial perfusion system for providing a physiological secretion necessary for functionality of a physiologic activity of a living-being host, the system comprising:

a) a housing having an inlet with an external opening thereto and an outlet with an external opening therefrom, the housing implantable at least partially within the host such that the inlet and outlet openings are placed in fluidic communication with peritoneal fluid within a peritoneal cavity of the host for receiving into and dispensing from the housing the peritoneal fluid;

b) a chamber disposed within the housing between the inlet and outlet and in communication therewith, the chamber having therein a plurality of physiologically active, autonomously and in concert functioning, live secretory cells for producing the physiological secretion;

c) a constantly operating two pump apparatus disposed for drawing initial peritoneal fluid through the inlet from the peritoneal cavity for contact with the physiologically active cells within the chamber for pick up of the physiological secretion, and for dispensing resulting peritoneal fluid bearing the physiological regulating secretion through the outlet and into the peritoneal cavity; and d) an inlet filter in operational communication with the external opening of the inlet and disposed upstream of the chamber, wherein the inlet filter comprises a tissue fluid sucking filter comprising a plurality of mesh woven polymer yarn and a size-exclusion membrane filter separated from each other by a capillary gap for peritoneal or other tissue fluid collection, filtration and prohibiting passage into the chamber of immune system agents and cells, immunoglobulins, and complement system components of the host.

In one aspect, the disclosure provides an implantable bioartificial perfusion system for providing a physiological secretion necessary for functionality of a physiologic activity of a living-being host, wherein the two pump apparatus are located upstream and downstream from the chamber, and wherein the pump apparatus uses electromagnetic, osmotic, or electro-osmotic force.

In another aspect, the disclosure provides an implantable bioartificial perfusion system for providing a physiological secretion necessary for functionality of a physiologic activity of a living-being host, further comprising an outlet filter in operational communication with the external opening of the outlet and disposed downstream of the chamber, the outlet filter having pores therethrough sized for prohibiting passage into the chamber of immune system agents, cells, immunoglobulins, and complement system components of the host.

In another embodiment, the disclosure provides an implantable bioartificial perfusion system for providing insulin as necessary for the metabolism of glucose within a living-being host, the system comprising:

a) a housing having an inlet with an external opening thereto and an outlet with an external opening therefrom, the housing implantable at least partially within the host such that the inlet and outlet openings are positionable in fluidic communication with tissue fluid of the host for receiving into and dispensing from the housing the tissue fluid;

b) a chamber disposed within the housing between the inlet and outlet and in communication therewith, the chamber having stack of several scaffold, double layer porous mesh matrices, therein a plurality of physiologically active, autonomously and in concert functioning, live secretory cells for producing insulin;

c) a constantly operating two pump apparatus for drawing initial tissue fluid through the inlet from the host for contact with the physiologically active cells within the chamber for pick up of insulin, and for dispensing the resulting tissue fluid bearing the insulin through the outlet and into the host; and d) an inlet filter in operational communication with the external opening of the inlet and disposed upstream of the chamber, the inlet filter comprising a tissue fluid sucking filter comprising a plurality of mesh woven polymer yarn and a size-exclusion membrane filter separated from each other by a capillary gap for peritoneal or other tissue fluid collection, filtration and prohibiting passage into the chamber of immune system agents and cells, immunoglobulins, and complement system components of the host.

In one aspect, the disclosure provides an implantable bioartificial perfusion system for providing insulin as necessary for the metabolism of glucose within a living-being host, wherein the two pump apparatus are located upstream and downstream from the chamber, and wherein the two pump apparatus uses electromagnetic, osmotic, or electro-osmotic force.

In another aspect, the disclosure provides an implantable bioartificial perfusion system for providing insulin as necessary for the metabolism of glucose within a living-being host, further comprising an outlet filter in operational communication with the external opening of the outlet and disposed downstream of the chamber, the outlet nanoporous membrane filter having pores therethrough sized for prohibiting passage into the chamber of immune system cells, immunoglobulins, and complement system components of the host.

In another embodiment, the disclosure provides an implantable bioartificial perfusion system for providing insulin necessary for carbohydrate metabolism within a living-being host, the system comprising:

a) a housing having an inlet with an external opening thereto and an outlet with an external opening therefrom, the housing implantable at least partially within the host such that the inlet and outlet openings are positionable in fluidic communication with peritoneal fluid inside a peritoneal cavity of the host for receiving into and dispensing from the housing the peritoneal fluid;

b) a chamber disposed within the housing between the inlet and outlet and in communication therewith, the chamber having stack of several scaffold, double layer porous mesh matrices, therein a plurality of physiologically active, autonomously and in concert functioning, live secretory cells for producing insulin, wherein the matrices are coated with autologous or allogeneic extracellular matrix (ECM) molecules and seeded with a plurality of ECM cells comprising fibroblasts and macrophages, and wherein two layers of each double matrix are kept at a certain distance from each other by spacers comprising polymer microspheres coated with ECM molecules;

c) a constantly operating two pump apparatus for drawing initial peritoneal fluid through the inlet from the peritoneal cavity for contact with the physiologically active cells within the chamber for pick up of regulating insulin, and for dispensing resulting peritoneal fluid bearing the insulin through the outlet and into the peritoneal cavity; and d) an inlet filter in operational communication with the external opening of the inlet and disposed upstream of the chamber, the inlet filter comprising a tissue fluid sucking filter comprising a plurality of mesh woven polymer yarn and a size-exclusion membrane filter separated from each other by a capillary gap for peritoneal or other tissue fluid collection, filtration and prohibiting passage into the chamber of immune system agents and cells, immunoglobulins, and complement system components of the host.

In one aspect, the disclosure provides an implantable bioartificial perfusion system for providing insulin necessary for carbohydrate metabolism within a living-being host, wherein the two pump apparatus are located upstream and downstream from the chamber and uses electromagnetic, osmotic, or electro-osmotic force or other force by a programmed controller disposed within the housing, and wherein the upstream pump apparatus is connected with a back-flush mechanism to clean/dislodge large molecules and/or cells clogging the size-exclusion membrane filter of the inlet and outlet.

In another aspect, the disclosure provides an implantable bioartificial perfusion system for providing insulin necessary for carbohydrate metabolism within a living-being host, further comprising an outlet filter in operational communication with the external opening of the outlet and disposed downstream of the chamber, the outlet filter having nanoporous membrane filter having pores therethrough sized for prohibiting passage into the chamber of immune system agents and cells, immunoglobulins, and complement system components of the host.

In another aspect, the disclosure provides an implantable bioartificial perfusion system for providing insulin necessary for carbohydrate metabolism within a living-being host, wherein the physiologically active secretory cells are pancreatic beta-islet cells provided from human allogenic and/or xenogenic and/or gene development technology sources.

In another aspect, the disclosure provides an implantable bioartificial perfusion system for providing insulin necessary for carbohydrate metabolism within a living-being host, wherein the physiologically active secretory cells are pancreatic islet beta cells.

In another aspect, the disclosure provides an implantable bioartificial perfusion system for providing insulin necessary for carbohydrate metabolism within a living-being host, wherein the controller is programmable and regulates administration of the back-flush cycles, and processes an alarm signal from a pH sensor followed by turning off the two pumps and turning on a sound and vibration alarm.

In another aspect, the disclosure provides an implantable bioartificial perfusion system for providing insulin necessary for carbohydrate metabolism within a living-being host, wherein the controller is integral with the housing.

In another embodiment, the disclosure provides an implantable bioartificial perfusion system for providing a physiological secretion necessary for functionality of a physiologic activity of a living-being host, the system comprising:

a) a housing having an inlet with an external opening thereto and an outlet with an external opening therefrom, the housing implantable at least partially within the host such that the inlet and outlet openings are positionable in fluidic communication with tissue fluid of the host for receiving into and dispensing from the housing the tissue fluid;

b) a chamber disposed within the housing between the inlet and outlet and in communication therewith, the chamber having stack of several scaffold, double layer porous mesh matrices, therein a plurality of physiologically active, autonomously and in concert functioning, live secretory cells for producing insulin, wherein the matrices are coated with autologous or allogeneic extracellular matrix (ECM) molecules and seeded with a plurality of ECM cells comprising fibroblasts and macrophages, and wherein two layers of each double matrix are kept at a certain distance from each other by spacers comprising polymer microspheres coated with ECM molecules;

c) a constantly operating two pump apparatus for drawing initial tissue fluid through the inlet from the host for contact with the physiologically active cells within the chamber for pick up of the physiological secretion, and for dispensing resulting tissue fluid bearing the physiological secretion through the outlet and into the host; and d) an inlet filter in operational communication with the external opening of the inlet and disposed upstream of the chamber, the inlet filter comprising a nanoporous membrane filter having pores therethrough sized for prohibiting passage into the chamber of immune system cells of the host.

In one aspect, the disclosure provides an implantable bioartificial perfusion system for providing a physiological secretion necessary for functionality of a physiologic activity of a living-being host, wherein the two pump apparatus are located upstream and downstream from the chamber and uses electromagnetic, osmotic, or electro-osmotic force or other force by a programmed controller disposed within the housing, and wherein the upstream pump apparatus is connected with a back-flush mechanism to clean/dislodge large molecules and/or cells clogging the size-exclusion membrane filter of the inlet and outlet.

In another aspect, the disclosure provides an implantable bioartificial perfusion system for providing a physiological secretion necessary for functionality of a physiologic activity of a living-being host, further comprising an outlet filter in operational communication with the external opening of the outlet and disposed downstream of the chamber, the outlet filter having nanoporous membrane filter having pores therethrough sized for prohibiting passage into the chamber of immune system agents and cells, immunoglobulins, and complement system components of the host.

In another aspect, the disclosure provides an implantable bioartificial perfusion system for providing a physiological secretion necessary for functionality of a physiologic activity of a living-being host, wherein the physiologically active secretory cells are pancreatic beta-islet cells provided from human allogenic and/or xenogenic and/or gene development technology sources.

Figure 1:
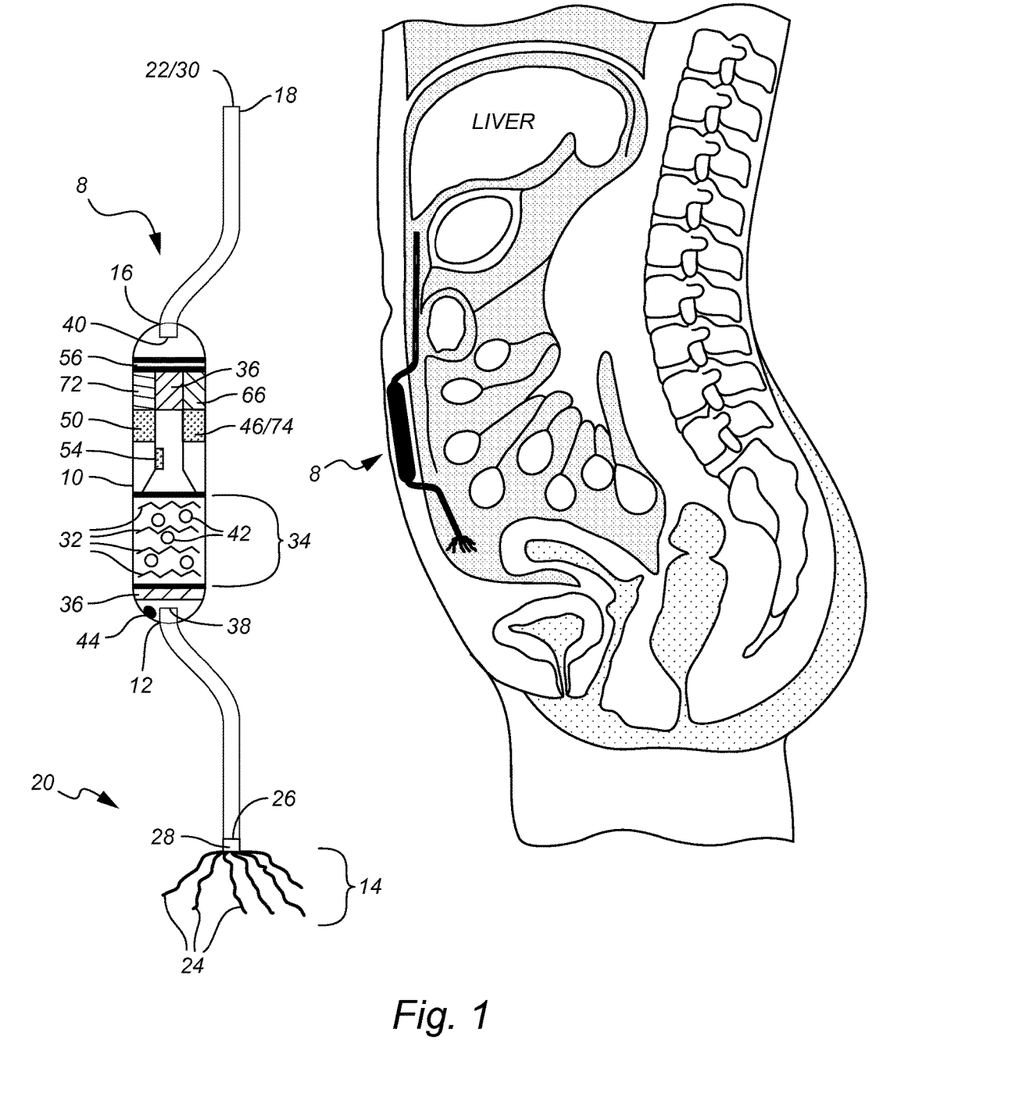
FIG. 1 is a cross-section view of an implantable bioartificial perfusion system implanted into a patient.
Figure 2:
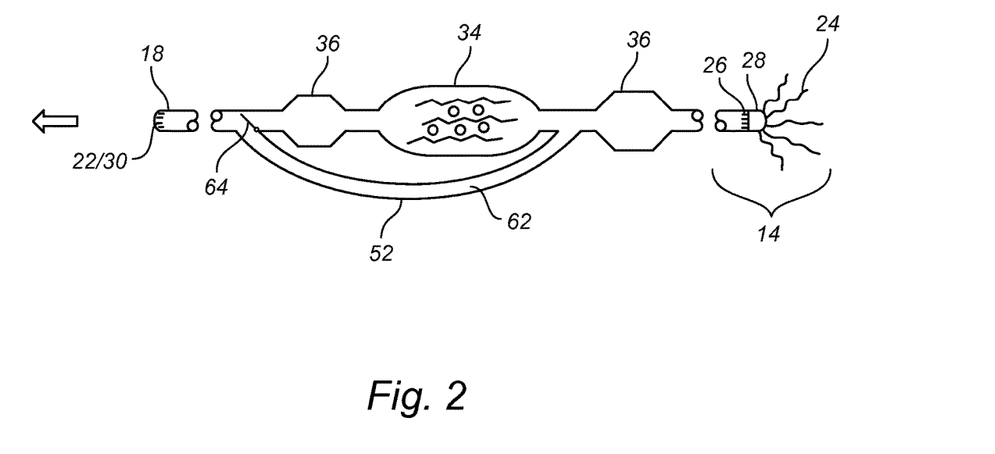
FIG. 2 is an illustration of the design and configuration of the external inlet tissue fluid sucking filter and external outlet nanoporous membrane filter and back-flush mechanism.
Figure 3:
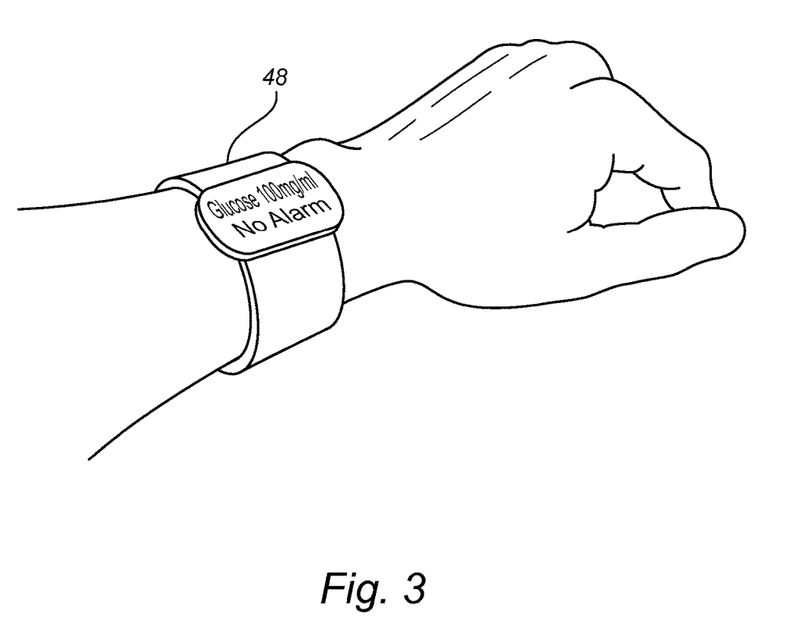
FIG. 3 is a view of the wrist, neck or belt wearable GUI display. The implant could also be made to communicate with what is currently termed a smart phone.

FIGS. 1-3 illustrate an embodiment of an implantable bioartificial perfusion system. The following chart summarizes the nonlimiting components of the implantable bioartificial perfusion system:

---

Implantable bioartificial perfusion system 8
Housing 10
Inlet 12
External inlet opening 14
Outlet 16
External outlet opening 18
Inlet external filter 20
Outlet external filter 22
Tissue fluid sucking filter 24
Inlet size-exclusion membrane filter 26
Capillary gap 28
Outlet size-exclusion membrane filter 30
Scaffold 32
Chamber 34
Two pump mechanisms 36
Inflow opening 38
Outflow opening 40
Spacers 42
Glucose sensor 44
Microprocessor 46
GUI display 48
Liquid flow sensor 50
Back-flush mechanism 52
Membrane pH sensor 54
Sound and/or vibration alarm 56
Shutters 58 and 60
Bypass channel 62
One-way valve 64
Rechargeable battery 66
Control unit 74

---

Referring to FIGS. 1-3, the implantable bioartificial perfusion system 8 includes a housing 10 with an inlet 12 with an external inlet opening 14 thereto; and an outlet 16 with an external outlet opening 18 therefrom, with inlet 12 and outlet 16 each having an external filter 20 and 22, respectively. The inlet external filter 20 is composed of two components: a tissue fluid sucking filter 24; and a size-exclusion membrane filter 26, separated from each other by a capillary gap 28. The outlet external filter 22 includes a size-exclusion membrane filter 30. The inlet external tissue fluid sucking filter 24 functions as a prefilter that controls the inflow of fluids and has pores/mesh sized to prevent the entry of larger immune cells of the host. Liquids have generally unimpeded access through the sucking filter 24. The tissue fluid sucking filter assures collection of the sufficient volume of the peritoneal fluid to feed the implantable bioartificial perfusion system and provides sufficient filtration of the cellular and humoral agents of the host immune system.

The inlet external filter 20 is composed of a tissue fluid sucking filter 24, made of a bunch or a plurality of mesh woven polymer yarn, and a size-exclusion membrane filter 26, separated from the bunch or plurality of mesh woven polymer yarn by a capillary gap 28 of about 25-50 µm, for peritoneal or other tissue fluid collection, filtration, protection against entry of immune system cells, immunoglobulins, and complement system components of a host living being. The bunch or plurality of mesh polymer yarn can collect peritoneal fluid from a high surface area of the peritoneal cavity parietal and visceral wall by means of capillary forces and deliver the fluid to the gap 28. The outlet external filter 22 includes a size-exclusion membrane filter 30, which may be a nanoporous membrane filter, to prevent immunogenic material of living cells, such as islet of Langerhans cells, in the housing 10 from leaking from the housing 10 into a host living being. The peritoneal fluid may be filtered through the membrane filter 30 and moved around the islets of Langerhans cells distributed inside a scaffold 32 in the islet chamber 34 and back to the peritoneal cavity through the outlet size-exclusion membrane filter 30 by an action of a two pump mechanisms 36. Both surfaces of the inlet membrane filter 26 and outlet membrane filter 30 may be coated with a protein resistant coating such as polyethylene glycol, linear poly (methyl glycerol) or linear polyglycerol. The scaffold 32 for islets allow for close emulation of the pancreatic environment. In particular, extracellular matrix (ECM) molecules can support the functional activity of the islet cells. The seeded fibroblasts can secret growth factors stimulating proliferation and activity of all five types of the islet cells. Seeded macrophages will clean/digest immunogenic material (dead cells and altered components of the ECM) that can potentially leak into the host system.

The housing 10 and the inlet external filter 20 and the outlet external filter 22 may be fabricated of a biocompatible polymer as known in the art.

Disposed within the housing 10 and in fluidic communication with the inlet 12 and outlet 16 is a chamber 34 having an inflow opening 38 and an outflow opening 40. Within the chamber 34 is housed a plurality of scaffolds 38 having three-dimensional porous matrices or double-layer matrices with spacers 42 there between, such as microspheres and the like, wherein a plurality of insulin and other hormone secretory cells such as provided by islet of Langerhans beta-cells and other islet cells, are disbursed among the stack of several matrices throughout the chamber 34. The scaffolds 32 provide the appropriate biomechanical, biochemical and biological conditions for islet cell proliferation and functional activity, uniform islet distribution, sufficient flow of the peritoneal liquid around each of the islets, and constant communication among islets. The matrices may be coated with autologous or allogeneic extracellular matrix (ECM) molecules and seeded with a plurality of ECM cells, for example, with fibroblasts and macrophages. The two layers of the matrices will be kept at a certain distance from each other by spacers 42 such as microspheres coated with ECM molecules. The plurality of the matrices enclosing islets will be stacked inside the islet chamber 34. Due to capillary forces of the material of the matrices, islets will be in a constant communication with the flowing peritoneal fluid.

Downstream of the chamber 34, is a electromagnetically, electro-osmotic, osmotic or other force driven two pump mechanism 36 for moving fluid (liquid) through the housing 10 and chamber 34 of the implantable bioartificial perfusion system 8. Due to capillary forces of the material of the mesh matrices of the scaffolds 32, the secretory cells are in constant fluidic communication with the moving peritoneal fluid. The two pump mechanisms 36 may be incorporated upstream and downstream of the chamber 34 to avoid any effect of the disrupted peritoneal fluid flow on the functionality of the islet cells.

The two pump mechanisms 36 provide a constant flow of the peritoneal fluid through the implantable bioartificial perfusion system for at least three years. The two pumps used for this purpose may be based on a variety of existing pumps and technologies in existence, such as electroosmotic, dielectrophoretic, micro sized mechanisms, piezoelectrics, etc. Depending on the pump type and action, the two pumps may be placed accordingly through the system at appropriate locations. Also contemplated is the use of one or two peristaltic pumps, with no moving parts to perform peristaltic motions necessary for transport of the peritoneal fluid through the system. The two pump mechanism 36 is an integrated part of the scaffold 32 or islet containing base unit.

Additionally, the housing 10 may include a miniature glucose sensor 44, such as a miniature amperometric self-powered continuous glucose sensor 44 that is placed at the inflow opening 38 of the chamber 34 for monitoring of the glucose concentration in the peritoneal fluid. The data may be delivered to the microprocessor 46, optionally with wireless capabilities. A glucose sensor 44 will control and assure proper operation of the system. If the concentration of the glucose is higher than normal level, it will set off an alarm and the doctor will decide either to increase flow velocity, or add insulin injections, or replace the implantable device. In case of a high glucose concentration the microprocessor 46 will first increase the flow rate via the two pump mechanisms 36 and if this does not help, a sound and vibration alarm inside and outside the implantable bioartificial perfusion system on a small graphical user interface (GUI) display 48.

A wireless GUI display 48 may be placed on a patient's wrist to allow implementing three levels of the system safety and discriminating among the corresponding levels of the alarm urgency. At the first level of the urgency (high glucose concentration in the tissue fluid), a doctor can observe patient, add lessened doses of the replacement therapy such as insulin injections, and wait for hormonal, metabolic or other profile stabilization. At the second level of the urgency (reduced flow rate of the tissue fluid), the doctor should replace the system because islet are about to die. At the last third level of the urgency (massive death of islets), the doctor should immediately see the patient to control potential hypoglycemia and to replace the system.

Additionally, the housing 10 encloses a miniature liquid flow sensor 50 to monitor the flow rate of tissue fluid such as peritoneal fluid flow rate and activate a back-flush mechanism 52 via microprocessor 46 when the flow rate is below an acceptable level. A miniature membrane pH sensor 54 may be used to detect a mass death of the islet of Langerhans cells when the pH≤7.35 and shut down the two pump mechanisms 36 and set off a sound and/or vibration alarm 56. This provides a simple, reliable and long lasting technique based on identification of the critical pH≤7.35 signaling death of the islet cells. In this case the doctor should immediately replace the implantable device.

The housing 10 may also encloses an electronic control circuit such as a microprocessor 46, optionally with wireless capabilities for monitoring of peritoneal fluid glucose level at the inflow opening 38 of the chamber 34, as well as pH value and flow velocity at the outflow opening 40 of the chamber 34. The microprocessor 46 may activate the back-flush mechanism 52 when the flow rate drops below an acceptable level and sets off a sound and/or vibration alarm 56 if the back-flush mechanism 52 does not work. Also, the microprocessor 46 can set off a sound and/or vibration alarm 56 if an abnormal glucose level cannot be resolved by increasing the flow rate of the tissue fluid. Finally, the microprocessor 46 can set off a sound and/or vibration alarm 56 in case of the massive cell death of the secretory cells. All normal as well as abnormal data and alarms can be wirelessly (Bluetooth) displayed on the small graphical user interface (GUI) display 48 placed on the patient's wrist or other convenient location or device. The GUI display 48 can communicate with microprocessor 46 and display an abnormal concentration of glucose in the peritoneal fluid, an abnormal reduction in the flow rate and a massive death of islets;—all accompanied by a sound and vibration alarm. Bluetooth, standardized as IEEE 802.15.1, is a wireless technology standard for exchanging data over short distances (using short-wavelength radio transmissions in the ISM band from 2400-2480 MHz) from fixed and mobile devices creating personal area networks (PANs) with high levels of security. The wireless connection can be one of several types, such us Bluetooth, wi-fi, any type of wireless connection, including an induction type of device or other developments. Each device will have a unique ID code so that the data can be uniquely identified with a particular patient, especially in the case where several patients, each using the device are in proximity of each other.

For redundancy, the implanted bioartificial perfusion system device is loaded with two to three times more islets than it is needed for treatment of the recipient's condition.

The housing 10 also encloses a back-flush mechanism 52 to clean/dislodge large molecules and/or cells clogging the size-exclusion membrane filters 26 and 30 of the inlet 12 and outlet 16, respectively. The back-flush mechanism 52 may be composed of a bypass channel 62, and a one-way valve 64 located downstream from the second pump before the outflow catheter. Periodically (for a short time) the downstream of the chamber pump may be stopped and the upstream of the chamber pump can be put in reverse to deflect the flow of the peritoneal fluid to the bypass channel 62, thus causing back-flash against inlet filter 26. The fluid flow through the bypass channel 62 produces suction on the outlet membrane filter 30, thus cleaning this filter 30 along with cleaning the inlet filter 26. The back-flush mechanism 52 cleaning of the nanoporous size-exclusion membrane of the inlet filter 26 and outlet filter 30 facilitates delivery of nutrients, oxygen, and glucose to the islet cells and insulin and other hormone distribution from the islet cells into the host system with the tissue fluid flow. The back-flush mechanism 52 may be activated by a control unit or microprocessor 46 when it receives a signal from a liquid flow sensor 50 indicating reduction of flow of peritoneal flow rate below an acceptable level.

The housing 10 may further include a self-charging mechanism (employed in electronic automatic quartz watches) that uses a weighted rotor to turn a tiny electrical generator, charging a rechargeable battery 72 when the patient with the implantable bioartificial perfusion system 8 is moving. The battery 72 powers a control unit 74, and the two pump mechanisms 36. Alternatively, the electronic control 74 and wireless circuits may be powered by a miniature or micro-sized rechargeable batteries 72. Included in the circuit is a means by which the batteries 72 may be inductively rechargeable, without having to remove the device from the patient. Alternatively, or in addition, the electronic control 74 and wireless circuits may be powered by a miniature or micro-sized rechargeable batteries 72. Included in the circuit is a means by which the batteries 72 may be inductively rechargeable, without having to remove the device from the patient.

As used herein, the term "biocompatible" includes any material that is compatible with living tissue or a living system by not being toxic or injurious and not causing immunological rejection. "Biocompatibility" includes the tendency of a material to be biocompatible. As used herein, the term "biocompatible" refers collectively to both the intact delivery device and its contents. Specifically, it refers to the capability of the implanted intact delivery device and its contents to avoid detrimental effects of the body's various protective systems and remain functional for a significant period of time. In addition to the avoidance of protective responses from the immune system, or foreign body fibrotic response, "biocompatible" also implies that no specific undesirable cytotoxic or systemic effects are caused by the delivery device and its contents such as would interfere with the desired functioning of the delivery device or its contents. The biocompatibility of the device is produced by a combination of factors. Of importance for biocompatibility and continued functionality are bioartificial perfusion system morphology, hydrophobicity and the absence of undesirable substances either on the surface of, or leachable from, the delivery device itself. Thus, brush surfaces, folds, interlayers or other shapes or structures eliciting a foreign body response are avoided. The bioartificial perfusion system—forming materials are sufficiently pure that unwanted substances do not leach out from the delivery device materials themselves.

First, the materials used to form the bioartificial perfusion system are substances selected based upon their ability to be compatible with, and accepted by, the tissues of the recipient of the implanted bioartificial perfusion system. Substances are used which are not harmful to the recipient or to the isolated biologically active cells. Second, substances used in preparing the biocompatible bioartificial perfusion system are either free of leachable pyrogenic or otherwise harmful, irritating, or immunogenic substances or are exhaustively purified to remove such harmful substances. Thereafter, and throughout the manufacture and maintenance of the bioartificial perfusion system prior to implantation, great care is taken to prevent the adulteration or contamination of the bioartificial perfusion system with substances which would adversely affect its biocompatibility. Third, the exterior configuration of the delivery device, including its texture, is formed in such a manner that it provides an optimal interface with the tissues of the recipient after implantation. This parameter will be defined in part by the site of implantation. For example, if the delivery device will reside in the peritoneal cavity of the recipient, its surface should be smooth. However, if it will be embedded in the soft tissues of the recipient, its surface can be moderately rough or stippled. A determining factor will be whether it is desirable to allow cells of the recipient to attach to the external surface of the delivery device or if such attachment must be avoided.

A variety of polymers are useful in producing the biocompatible housing, chamber, scaffold and semi-permeable membrane for the nanofilters of the present invention. They include, but are not limited to polyalginate, polyvinylchloride, polyvinylidene fluoride, polyurethane isocyanate, cellulose acetate, cellulose diacetate, cellulose triacetate, cellulose nitrate, polysulfone, polystyrene, polyurethane, poly40 vinyl alcohol, polyacrylonitrile, polyamide, polymethylmethacrylate, polytetrafluoroethylene, and polyethylene oxide. In addition, useful semi-permeable membranes may be produced from a combination of such polymers.

As to the pores size of the nanofilters, delivery devices with pores having a molecular weight exclusion of from about 50 kD to about 300 kD may be useful, with those having pores with a molecular weight cut off of from about 25 kD to about 200 kD also being useful. Other pore configurations and/or dimensions are possible without departure from the scope of the present invention.

In an embodiment, the viable cells enclosed within the bioartificial perfusion system are eukaryotic cells, for example, mammalian cells. Any cells that secrete the biologically active agent that is therapeutic to a subject malady may be incorporated into the system of the invention. These cells may be autologous or allogeneic or xenogeneic, or progenitor cells, e.g., stem cells and other pluripotent cells. Additionally or alternatively, cells that secrete a biologically active agent that is prophylactic to a subject malady may be incorporated into the system of the invention. Further, any cells which have been genetically engineered to express a desired active agent, growth factor, and/or their agonists, precursors, derivatives, analogs, or fragments thereof, or other active agents having similar effector activities may also be useful in practicing this invention. Additionally, growth factors or growth regulatory substances, and/or a population of feeder or accessory cells may be co-isolated within the bioartificial perfusion system. For example, beta cells within islets of Langerhans may be co-isolated with fibroblasts accessory cells.

It is contemplated, however, that the bioartificial perfusion system may be used to deliver into the systemic circulation any molecule that can be produced and secreted from a viable cell. Although single cell types that produce and secrete a single preselected molecule may be used in the invention, it is understood that cells belonging to a particular cell type that produce and secrete a plurality of preselected molecules likewise may be used in the practice of the present invention. Similarly, it is contemplated that a plurality of cell types, wherein cells belonging to each cell type produce and secrete different preselected molecules, may be combined in the chamber 34 thereby to produce a device that delivers a desirable combination of preselected molecules into the circulation.

An important component of the bioartificial perfusion system includes the internal cell-supporting matrix or scaffold. The scaffold defines the microenvironment for the immune-isolated cells, keeps the cells well distributed within the chamber 34 and provides adequate microcirculation of the tissue fluid. One advantage of the proposed system is its ability to provide microcirculation of the peritoneal fluid of the host around each "naked" islet along with complete immunoisolation and multi-level safety control. The optimal internal scaffold for a particular cell bioartificial perfusion system is highly dependent on the cell type. For example, while adherent cells often lie on a solid surface, suspension cells may lie upon a hydrophilic lightly cross-linked hydrogel as a matrix material.

In the absence of a scaffold, adherent cells aggregate to form clusters. When the clusters grow too large, they typically develop a central necrotic core. Dying cells accumulate around the core and, upon lysing, release factors detrimental to the health of neighboring cells. The lysed cell fragments are also transported to the host environment, there eliciting an antigenic response.

Several types of prior art devices have attempted to solve these problems, meeting with mixed results. For example, the prior art includes the use of bonded fiber structures for cell implantation (U.S. Pat. No. 5,512,600) and the use of biodegradable polymers as scaffolds for organ regeneration such as, for example, liver, pancreas, and cartilage. The use of biodegradable polymers for use as scaffolds in organ regeneration is reviewed by Cima et al., BIOTECH. BIOENG, 38: 145-58 (1991). In these prior art works, biodegradable fiber tassels and fiber-based felts (i.e., non-woven materials) were used as scaffolds for transplanted cells. One drawback to the use of biodegradable polymers, particularly polymers of poly(lactic acid) PLA, poly(lacticcoglycolic acid) PLGA, poly(glycolic acid) PGA, and their equivalents, is that upon degradation, they release lactic and/or glycolic acid, which are toxic to surrounding tissue. As the polymers degrade, they break down to first low molecular weight oligomers and then to the acids, causing a rapid increase in acid released into the surrounding tissue. This rise in acid concentration in vivo in the local environment of the implant can induce an inflammatory response or tissue necrosis. Foam scaffolds have also been used in the art to provide surfaces onto which transplanted cells may adhere. Foam scaffolds, however, have random flat surfaces and do not provide a linear template for reorganization. Some cell types use such a template for organization into physiological three-dimensional orientation. Prior art also includes woven mesh tubes used as vascular grafts. Although cells may be seeded onto these woven tubes for improved biocompatibility, these tubes function primarily as vascular conduits and not cell scaffolds. Thus, a need exists in the art for a non-degradable scaffold or framework system to provide an ordered three-dimensional close to natural environment for cells which use such an environment to grow and proliferate within bioartificial perfusion system.

Certain delivery device geometries have also been found to specifically elicit foreign body fibrotic responses and should be avoided. Thus delivery devices should not contain structure having interlayers such as brush surfaces or folds. In general, opposing delivery device surfaces or edges either from the same or adjacent delivery devices should be at least 1 mm apart, or greater than 2 mm, or greater than 5 mm. Some embodiments include cylinders, "U"-shaped cylinders, and flat sheets or sandwiches. The surrounding or peripheral region (jacket) of the biocompatible delivery device can optionally include substances which decrease or deter local inflammatory response to the implanted delivery device.

An outer housing wall may be a polymer material and may include a surfactant, an anti-inflammatory agent, angiogenic factors, and/or an anti-oxidant. The specific type of polymer, surfactant, or other additive may depend on the material to be encapsulated and the configuration of the bioartificial perfusion system. Exemplary anti-inflammatory agents include, but are in no way limited to, corticoids such as cortisone and ACTH, dexamethasone, cortisol, interleukin-I and its receptor antagonists, and antibodies to TGF-beta, to interleukin-I (IL-I), and to interferon-gamma. Exemplary surfactants include, but are in no way limited to, Triton-X 100 from Sigma Chemicals, and Pluronics P65, P32, and P I 8. Exemplary anti-oxidants include, but are in no way limited to, vitamin C (ascorbic acid) and vitamin E. Exemplary angiogenic factors include, but are in no way limited to, fibroblast growth factor and nerve growth factor.

The invention provides an internal filamentous cell-supporting matrix or scaffolding comprising a plurality of filaments, for example, they may be spun into one or more yarns, or alternatively woven into one or more mesh components. The cell scaffold, in the device of the invention advantageously provides cells with a template for cellular organization in a three-dimensional orientation resembling their typical physiological shape.

In one embodiment, the filamentous cell-supporting scaffold is made from any substantially non degradable biocompatible material. For example, the material can be acrylic, polyester, polyethylene, polypropylene, polyacetonitrile, polyethylene terephthalate, nylon, polyamides, polyurethanes, polybutylester, silk, cotton, chitin, carbon, or biocompatible metals. The fibers known to the state of the art are substantially non-degradable and so do not release by-products into the host. Moreover, the yarn and mesh matrices used in the invention have the following advantages over prior art hydrogel matrices: (1) they provide a physical surface onto which extracellular matrix molecules may be attached; (2) they allow adherent cell types to attach and lay down their own extracellular matrix material; (3) the yarn or mesh matrix can keep cells distributed more evenly both longitudinally and transversely and thus prevent cell clumping which leads to subsequent necrotic core formation; (4) they offer greater biological stability than hydrogel materials and have a long history of implant use as vascular grafts and suture materials.

In another embodiment, the core scaffold contains a plurality of monofilaments. In one example, the monofilaments are twisted into yarn. In another example, the plurality of monofilaments or the yarn is woven into mesh. In another embodiment, the scaffolding is coated with extracellular matrix (ECM) molecules. Suitable ECM molecules may include, for example, collagen, laminin, and fibronectin. The present invention provides several advantages over the prior art. The ECM is seeded with a plurality of cells, which are naturally present in the tissue that is simulated, at minimum with two types of cells: fibroblasts and macrophages. The fibroblasts will reconstitute and maintain ECM and stimulate growth and proliferation of the main cells. The macrophages will scavenge dead cells and deteriorating material thus preventing antigenic substances from leaking to the host system. Also, using capillary properties of the woven mesh or 3D polymer scaffold having interconnected network of cells and pores will provide a uniform flow of the tissue fluid around each cell aggregate inside the chamber 34. Finally, the scaffold stack will render appropriate biomechanical and biochemical conditions for islet cells proliferation and functional activity.

Operability is here non-limitedly exemplified in the physiologically beneficial delivery-on-demand of insulin for glucose metabolism within a patient suffering from Type I diabetes. Particularly, the system housing functions in the capacity of an artificial pancreas and is implanted at a site within the peritoneal cavity such that peritoneal fluid can enter the housing. The housing can be located subcutaneously and be anchored to the anterolateral region of the iliac crest bone by a bone anchor system as known in the art with catheter penetration through the peritoneal fascia and into the peritoneal cavity. This placement permits relatively easy, rapid, and complete retrieval in the event of any implant failure or malfunction. Implantation into the anterolateral subcutane abdominal region is carried out under local anesthesia. It is to be noted that peritoneal fluid is chosen for insulin-need determination because a change of glucose concentration in peritoneal fluid is in the same direction, same amount, and relatively same time factor as in blood. The peritoneal fluid travels through the inlet filter, inlet opening to the chamber 34 by pumping action of the two pump mechanisms 36 that provides continuous microcirculation of the fluid in contact with insulin secretory cells, which can be present as beta-cells of islets of Langerhans.

In one embodiment, groups of bare not-encapsulated islets each having a diameter from about 50 to about 200 microns, with total count for the entire chamber of at least about 1,000,000 islets are uniformly dispersed inside porous three-dimensional soft scaffold. Each scaffold matrix may be fabricated of biocompatible and stable polymer mesh matrices coated with autologous or allogeneic extracellular matrix (ECM) molecules seeded with a plurality of ECM cells in particularly with fibroblasts and macrophages for housing the secretory cells. The islets will be distributed either inside pores of each layer of the matrix or between two layer of the matrices. The two layers will be kept at a certain distance from each other by spacers such as microspheres coated with ECM molecules. The plurality of the single or double matrices enclosing islets will be stacked inside the islet chamber. Movement of the peritoneal fluid continues through the chamber for contact with each porous layer or double layer scaffolds/matrix bearing the insulin secretory cells, as these secretory cells naturally react to the glucose level of the peritoneal fluid and naturally secrete insulin into the peritoneal fluid as determined by the secretory cells to be needed for proper glucose metabolism. Additionally, oxygen and nutrients are passed to the secretory cells while metabolic waste from the secretory cells passes into the peritoneal fluid. Upon completion of travel through the chamber, the peritoneal fluid moves to the outlet, through the, external outlet opening and outlet nanoporous membrane filter for final reintroduction into the peritoneal cavity and final delivery to the circulatory system through normal and on-going routing for insulin delivery and use as well as elimination of secretory-cell waste products. Secretory-cell life spans are, of course, dependent upon a number of factors including proper nutrition and oxygen delivery, appropriate biomechanical and biochemical conditions of the scaffold, waste product removal, and extent of secretion called for by the host being. When cell effectiveness diminishes or ceases, however, the implantable bioartificial perfusion system is relatively easily retrieved to be replaced by a new system.

As is apparent from the above description, the perfusion system here defined bioartificially emulates a naturally occurring secretion system by providing live secretion-producing cells for sensing and producing secretions at levels naturally determined because of such live authenticity. In addition to such implantation of secretion-producing so cells, other media, including drugs, medicines, and/or enzymes, for treating or preventing diseases in accord with physiological demands, can likewise be administered by employing the system here described and within which the chosen media is placed. Thus, while these illustrative embodiments of the invention have been described in detail herein, it is to be understood that the inventive concepts may be otherwise variously embodied and employed and that the appended claims are intended to be construed to include such variations except insofar as limited by the prior art.

What is claimed is:

1. An implantable bioartificial perfusion system for providing a physiological regulating secretion necessary for functionality of a physiologic activity of a living-being host, the system comprising:

a) a housing having an inlet with an external opening thereto and an outlet with an external opening therefrom, the housing implantable at least partially within the host such that the inlet and outlet openings are positionable in fluidic communication with tissue fluid of the host for receiving into and dispensing from the housing the tissue fluid;

b) a chamber disposed within the housing between the inlet and outlet and in communication therewith, the chamber having a plurality of scaffolds having three-dimensional porous matrices with polymer microsphere spacers coated with extracellular matrix (ECM) molecules there between, wherein a plurality of physiologically active, autonomously and in concert functioning, live secretory cells for producing the physiological regulating secretion are disbursed among the porous matrices throughout the chamber, wherein the matrices are coated with autologous or allogeneic extracellular matrix (ECM) molecules and seeded with a plurality of ECM cells comprising fibroblasts and macrophages, and wherein layers of each matrix are kept at a certain distance from each other by the polymer microsphere spacers;

c) a constantly operating two pump apparatus for drawing initial tissue fluid through the inlet from the host for contact with the physiologically active cells within the chamber for pick up of the physiological regulating secretion, and for dispensing resulting tissue fluid bearing the physiological regulating secretion through the outlet and into the host; and d) an inlet filter in operational communication with the external opening of the inlet and disposed upstream of the chamber, wherein the inlet filter comprises a plurality of mesh woven polymer yarn to collect peritoneal fluid from a high surface area of the parietal peritoneum and visceral peritoneum by means of capillary forces and a size-exclusion membrane filter separated from the plurality of mesh woven polymer yarn by a capillary gap for prohibiting passage into the chamber of immune system cells of the host.

2. The implantable bioartificial perfusion system of claim 1, wherein the two pump apparatus is located upstream and downstream from the chamber, and wherein the two pump apparatus uses electromagnetic, osmotic, or electro-osmotic force.

3. The implantable bioartificial perfusion system of claim 1, further comprising an outlet filter in operational communication with the external opening of the outlet and disposed downstream of the chamber, wherein the outlet filter comprises pores therethrough sized for prohibiting passage into the chamber of immune system cells of the host.

4. An implantable bioartificial perfusion system for providing a physiological regulating secretion necessary for functionality of a physiologic activity of a living-being host, the system comprising:

a) a housing having an inlet with an external opening thereto and an outlet with an external opening therefrom, the housing implantable at least partially within the host such that the inlet and outlet openings are positionable in fluidic communication with peritoneal fluid within a peritoneal cavity of the host for receiving into and dispensing from the housing the peritoneal fluid;

b) a chamber disposed within the housing between the inlet and outlet and in communication therewith, the chamber having a plurality of scaffolds having three-dimensional porous matrices with polymer microsphere spacers coated with extracellular matrix (ECM) molecules there between, wherein a plurality of physiologically active, autonomously and in concert functioning, live secretory cells for producing the physiological regulating secretion are disbursed among the porous matrices throughout the chamber, wherein the matrices are coated with autologous or allogeneic extracellular matrix (ECM) molecules and seeded with a plurality of ECM cells comprising fibroblasts and macrophages, and wherein layers of each matrix are kept at a certain distance from each other by the polymer microsphere spacers;

c) a constantly operating two pump apparatus disposed for drawing initial peritoneal fluid through the inlet from the peritoneal cavity for contact with the physiologically active cells within the chamber for pick up of the physiological regulating secretion, and for dispensing resulting peritoneal fluid bearing the physiological regulating secretion through the outlet and into the peritoneal cavity; and d) an inlet filter in operational communication with the external opening of the inlet and disposed upstream of the chamber, wherein the inlet filter comprises a tissue fluid sucking filter comprising a plurality of mesh woven polymer yarn and a size-exclusion membrane filter separated from each other by a capillary gap for peritoneal or other tissue fluid collection, filtration and prohibiting passage into the chamber of immune system agents and cells, immunoglobulins, and complement system components of the host.

5. The implantable bioartificial perfusion system of claim 4, wherein the two pump apparatus is located upstream and downstream from the chamber, and wherein the two pump apparatus uses electromagnetic, osmotic, or electro-osmotic force.

6. The implantable bioartificial perfusion system of claim 4, further comprising an outlet filter in operational communication with the external opening of the outlet and disposed downstream of the chamber, the outlet filter having pores therethrough sized for prohibiting passage into the chamber of immune system agents, cells, immunoglobulins, and complement system components of the host.

7. An implantable bioartificial perfusion system for providing insulin as necessary for the metabolism of glucose within a living-being host, the system comprising:

a) a housing having an inlet with an external opening thereto and an outlet with an external opening therefrom, the housing implantable at least partially within the host such that the inlet and outlet openings are positionable in fluidic communication with tissue fluid of the host for receiving into and dispensing from the housing the tissue fluid;

b) a chamber disposed within the housing between the inlet and outlet and in communication therewith, the chamber having a plurality of scaffolds having three-dimensional porous matrices with polymer microsphere spacers coated with extracellular matrix (ECM) molecules there between, wherein a plurality of physiologically active, autonomously and in concert functioning, live secretory cells for producing insulin are disbursed among the porous matrices throughout the chamber, wherein the matrices are coated with autologous or allogeneic extracellular matrix (ECM) molecules and seeded with a plurality of ECM cells comprising fibroblasts and macrophages, and wherein layers of each matrix are kept at a certain distance from each other by the polymer microsphere spacers;

c) a constantly operating two pump apparatus for drawing initial tissue fluid through the inlet from the host for contact with the physiologically active cells within the chamber for pick up of insulin, and for dispensing the resulting tissue fluid bearing the insulin through the outlet and into the host; and d) an inlet filter in operational communication with the external opening of the inlet and disposed upstream of the chamber, the inlet filter comprising a tissue fluid sucking filter comprising a plurality of mesh woven polymer yarn and a size-exclusion membrane filter separated from each other by a capillary gap for peritoneal or other tissue fluid collection, filtration and prohibiting passage into the chamber of immune system agents and cells, immunoglobulins, and complement system components of the host.

8. The implantable bioartificial perfusion system of claim 7, wherein the two pump apparatus is located upstream and downstream from the chamber, and wherein the two pump apparatus uses electromagnetic, osmotic, or electro-osmotic force.

9. The implantable bioartificial perfusion system of claim 7, further comprising an outlet nanoporous membrane filter in operational communication with the external opening of the outlet and disposed downstream of the chamber, the outlet nanoporous membrane filter having pores therethrough sized for prohibiting passage into the chamber of immune system cells, immunoglobulins, and complement system components of the host.

* * * * *